United States Patent [19]
Dong et al.

[11] Patent Number: 6,153,678
[45] Date of Patent: Nov. 28, 2000

[54] INJECTION-MOLDABLE COMPOSITION AND ARTICLE OF MANUFACTURE COMPRISING SAME

[75] Inventors: Liang-Chang Dong, Sunnyvale; Crystal Pollock, Mountain View; Patrick S.-L. Wong, Burlingame; Keru O. Shafi, Hayward; Vincent J. Ferrari, Foster City; Ted Smith, Castro Valley, all of Calif.

[73] Assignee: Alza Corporation, Mountain View, Calif.

[21] Appl. No.: 09/167,372

[22] Filed: Oct. 6, 1998

Related U.S. Application Data

[60] Provisional application No. 60/060,976, Oct. 6, 1997.

[51] Int. Cl.$^7$ ....................... C08K 5/11
[52] U.S. Cl. ........................ 524/315
[58] Field of Search ................ 524/315

[56] References Cited

U.S. PATENT DOCUMENTS

| | | | |
|---|---|---|---|
| 3,865,108 | 2/1975 | Hartop | 128/260 |
| 4,207,893 | 6/1980 | Michaels | 128/260 |
| 4,612,008 | 9/1986 | Wong et al. | 604/892 |
| 4,746,509 | 5/1988 | Haggiage | 424/449 |
| 5,202,205 | 4/1993 | Malhota | 430/17 |
| 5,232,705 | 8/1993 | Wong et al. | 424/473 |
| 5,312,388 | 5/1994 | Wong et al. | 604/892.1 |

OTHER PUBLICATIONS

Drugs, vol. 30, pp. 333–354, (1985).
Encyclopedia of Polymer Science and Engineering, vol. 8, pp. 102–138 (1987).
Controlled Release System, vol. 11, p. 46 (1988), CRC Press, Inc. (Fabrication Technology).
Pharmacotheraply, vol. 8, pp. 147–157 (1988).
Encyclopedia of Polymer Science and Engineering, Supp. vol. pp. 702–711, (1989), Interscience Publ.

*Primary Examiner*—Paul R. Michl
*Attorney, Agent, or Firm*—John A. Dhuey; Steven F. Stone

[57] ABSTRACT

Polymeric compositions are disclosed comprising a poly(caprolactone), a poly(alkylene oxide), a poly(oxyethylenated fatty acid ester), or a poly(oxyethylenated fatty acid), or a poly(oxyethylene-co-oxypropylene).

8 Claims, 4 Drawing Sheets

INJECTION-MOLDABLE COMPOSITION AND ARTICLE OF MANUFACTURE COMPRISING SAME

CROSS-REFERENCE TO RELATED APPLICATION

This application claims the benefits of provisional application U.S. Serial No. 60/060,976 filed Oct. 6, 1997 under 35 U.S.C. §119(e).

FIELD OF THE INVENTION

This invention pertains to both a novel and useful injection-moldable composition. More specifically, the invention concerns an injection-moldable composition comprising a poly(caprolactone), a poly(alkylene oxide), and either a poly(oxyethylated carboxylic acid or the ester thereof) or a poly(oxyethylene-co-oxypropylene). The invention relates also to an injected-molded membrane and to a dosage form manufactured comprising the injection-molded membrane provided by the injection-moldable composition of this invention.

BACKGROUND OF THE INVENTION

Currently, many articles of manufacture such as dosage forms for delivering a drug involve a process of membrane coating to a core of drug, where an organic solvent, for example, acetone and/or methylene chloride is used for applying the membrane. Unfortunately, there are serious limitations with organic solvent coating processes. That is, the organic solvents are expensive, they are explosive, and they can cause environmental concerns. Moreover, organic solvent coating with a mixed solvent system is accompanied by inherent different evaporation rates of the solvent components, that makes it difficult to form uniform membranes. Then, it becomes time-consuming and costly to optimize coating conditions for scale up. These prior art processes might give rise to a lack of uniform membranes and these variances in membrane morphology often subtract from producing quality articles of manufacture.

In the U.S. Pat. No. 5,614,578, patentees Dong, Wong, Pollock, and Ferrari made available to the injection-molding and membrane arts inventive compositions for forming injection-moldable membrane comprising poly (caprolactone), poly(alkylene oxide), and poly(ethylene glycol). These compositions are successful for manufacturing articles of commerce such as dosage forms by injection-molding using a cold-runner mold. However, in hot-runner mold operations, serious technical problems are encountered as the compositions exhibits phase-separation into its components leading to poor mechanical properties and reduction of manufacturing speed.

It will be appreciated by those skilled in the injection-molding art that a critical need exists for a novel polymeric composition for injection-molding that is free from the problems associated with the prior art. Likewise, it will be appreciated by those skilled in the art, that if a novel composition is provided for injection-molding a membrane for manufacturing a dosage form, such a composition would represent a positive advancement and an unexpected improvement in both the polymer and dosage form arts.

OBJECTS OF THE INVENTION

Accordingly, in view of the above presentation, it is an immediate object of this invention to provide a novel composition indicated for injection-molding by standard manufacturing techniques that overcomes the shortcomings and the disadvantages known to the prior art.

Another object of the invention is to provide a ternary injection-moldable compositions essentially-free of organic solvents.

Another object of the present invention is to provide an initially ternary injection-moldable composition homogenized into a homogenous composition for manufacturing a membrane useful for making available commercial articles of manufacture.

Another object of the invention is to make a composition comprising two poorly miscible polymers and a third polymer that exhibits miscibility with the former two polymer to produce a more compatible polymer composition.

Another object of the invention is to make available a composition produced by the compatibilization of two polymers by a different polymer compatibilizer to provide a more compatible polymeric composition.

Another object of the invention is to provide novel membranes made by injection-molding a homogenous, single-phase composition, wherein the membrane possess permeability to water, serves as the rate-controlling membrane for delivery system, and possess mechanical properties useful for manufacturing a dosage form.

Another object of the invention is to provide a composition with thermoplastic properties useful for injection-molding items of health and for the elimination of disease.

Another object of the invention is to provide a composition for an injection-molding process for manufacturing membranes that can be used in the mass-commercial production of dosage forms.

Other objects, features, aspects, and advantages of this invention will be more apparent to those versed in the thermoplastic-molding art and in this dispensing art from the following detailed specification taken in conjunction with the accompanying claims.

BRIEF DESCRIPTION OF DRAWING FIGURES

DESCRIPTION OF THE INVENTION

Figure 1:
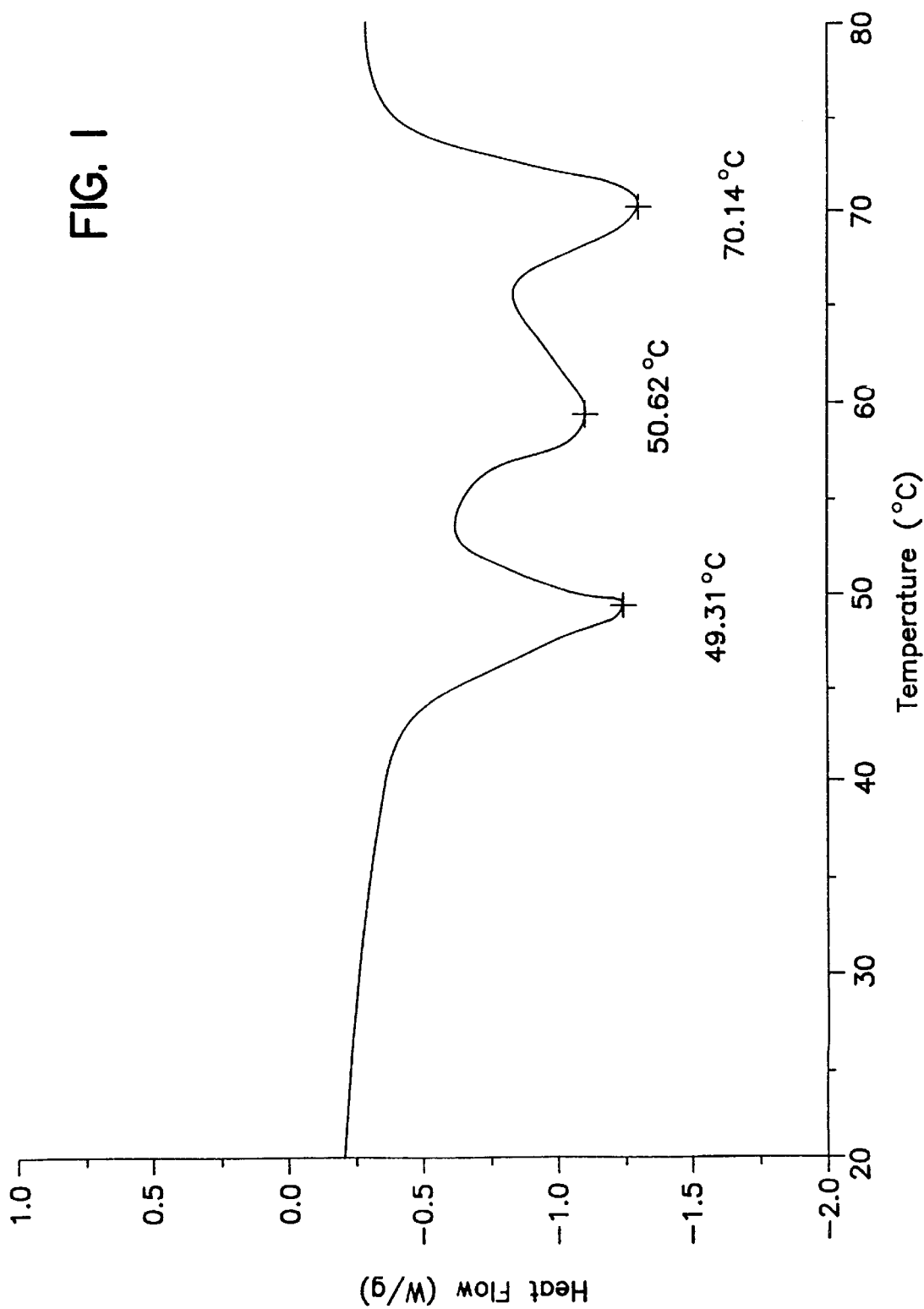
FIG. 1 depicts the differential scanning colorimetry for a polymer composition that exhibits three individual melting peaks, indicating phase separation.

According to the mode and the manner of this invention, novel and useful polymer compositions are provided for injection-molding into novel and useful membranes. The membranes can be designed, shaped, and formed into articles of manufacture, including dosage forms for delivering a drug. The polymer compositions comprise a poly (caprolactone) of 10,000 to 1,250,000 number-average molecular weight commercially available from Union Carbide Corporation, Danbury, Conn.; and a poly(alkylene oxide) of 40,000 to 10,000,000 weight-average molecular weight, as represented by poly(ethylene oxide) available from the Union Carbide Corporation. The polymer composition comprises also a poly(oxyethylenated fatty acid), or a poly(oxythylenated fatty acid ester). Representative thereof comprise poly(oxyethylene lauric acid) comprising 10 to 46 moles of ethylene oxide, poly(oxyethylene myristic acid) comprising 11 to 49 moles of ethylene oxide, poly (oxyethylene oleic acid) comprising 5 to 10 moles of ethylene oxide, poly(oxyethylene palmitic acid) comprising 8 to 39 moles of ethylene oxide, poly(oxyethylene stearic acid) comprising 5 moles to 50 moles of ethylene oxide, poly(oxyethylene 10 to 46 laurate), poly(oxyethylene 10 to 49 myristate), poly(oxyethylene 5 to 10 oleate), poly (oxyethylene 8 to 39 palmitate), and poly(oxyethylene 5 to 50 stearate). The polymer composition may comprise poly (oxyethylene-co-oxypropylene). The poly(oxyethylene)-co-poly(oxypropylene) block copolymers are known as Pluronic copolymers: Pluronic F-38, Pluronic F-68, Pluronic L-44, Pluronic L-62, Pluronic 64, Ploronic F-108 and Pluronic F-127. The block copolymers comprise a molecular weight of 1,100 to 25,000. The poly(oxyethylene)poly (oxypropylene) block copolymers are known also as poly (oxyethylene)poly(oxypropylene) block copolymers. They are available under the trademark Pluronic from BASF Corporation, Parsippany, N.J. The poly(oxyethylene fatty acid and esters) are commercially available from Atlas Chemical Industries, Wilmington, Del.; Armour Industries, Chicago, Ill.; and GAF Corporation, New York, N.Y. The polymer composition comprises 40 to 85 wt % poly (caprolactone), 5 to 40 wt % poly(alkylene oxide) and 2 to 20 wt % poly(oxyethylenated fatty acid or ester), or poly (oxyethylene-co-oxypropylene), with the total weight in the composition equal to 100 wt %.

The following examples are illustrative of the present invention, and they should not be considered as limiting the scope of the invention in any way, as these examples and other equivalents thereof will become apparent to those versed in the art in light of the present disclosure and the accompanying claims.

EXAMPLE 1

Figure 2:
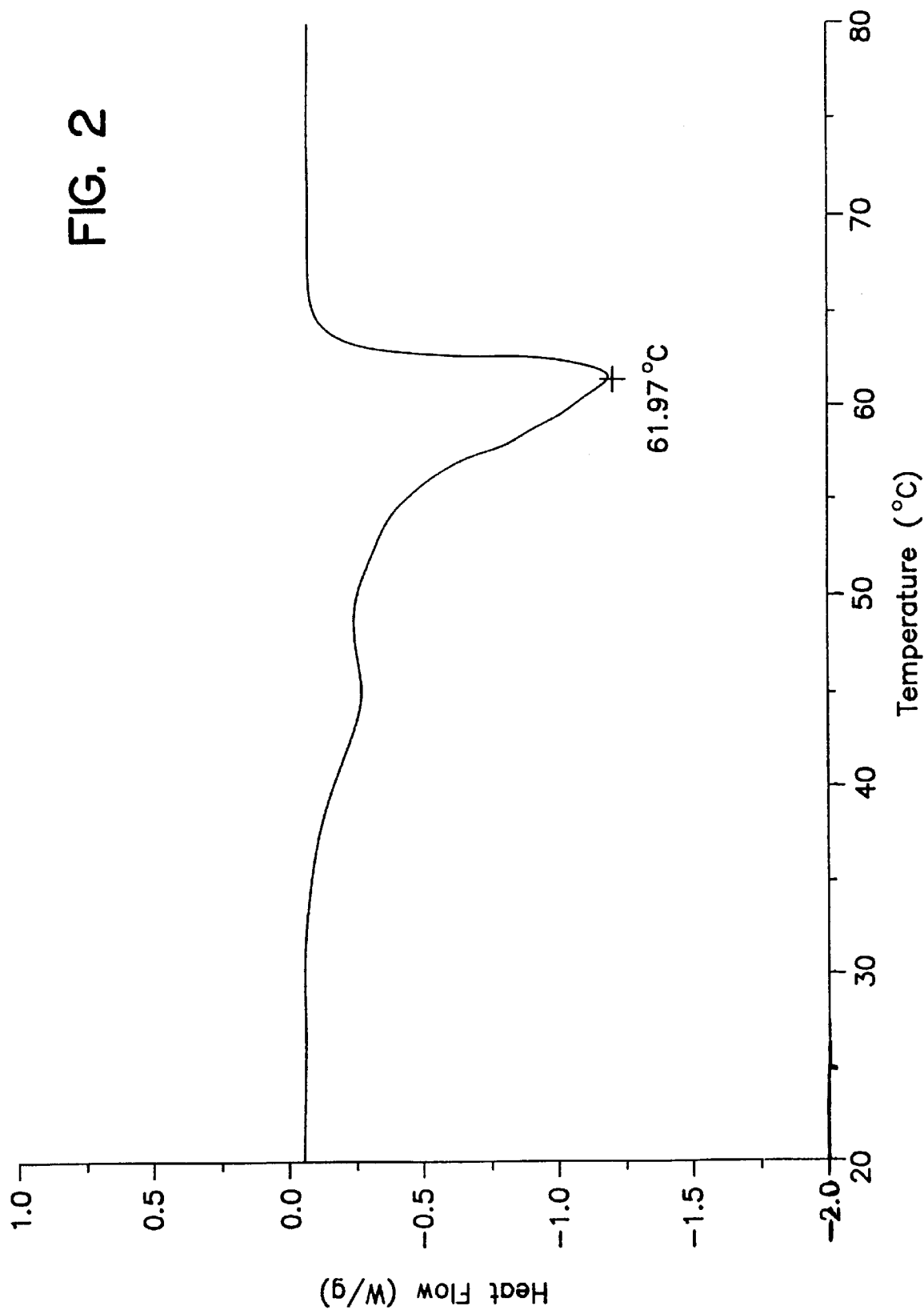
FIG. 2 depicts the differential scanning colorimetry for a polymer composition that exhibits a single melting peak, free of separation.
Figure 3:
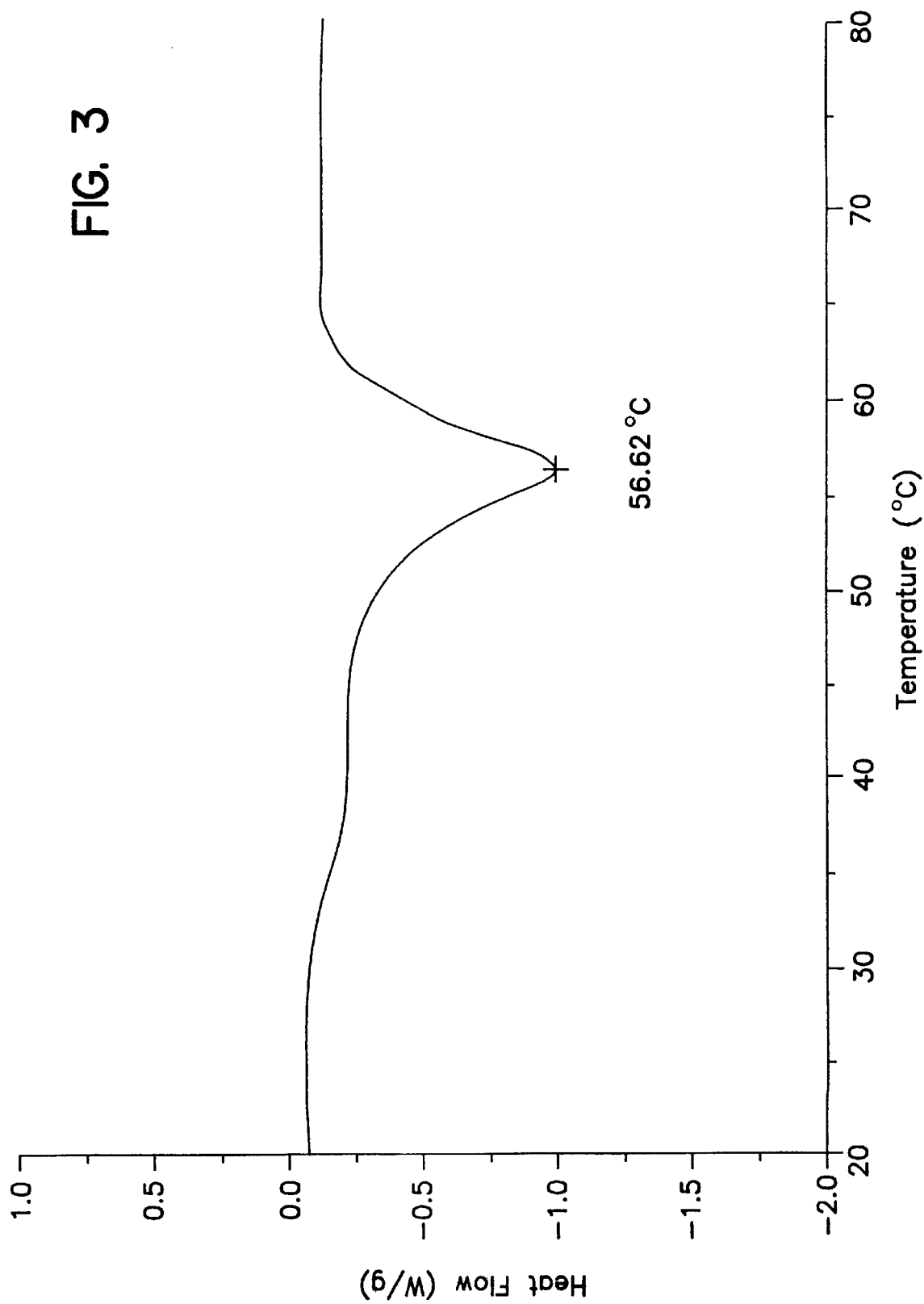
FIG. 3 depicts the differential scanning colorimetry for a polymer composition with a single melting peak free of phase separation tested at an elevated temperature.
Figure 4:
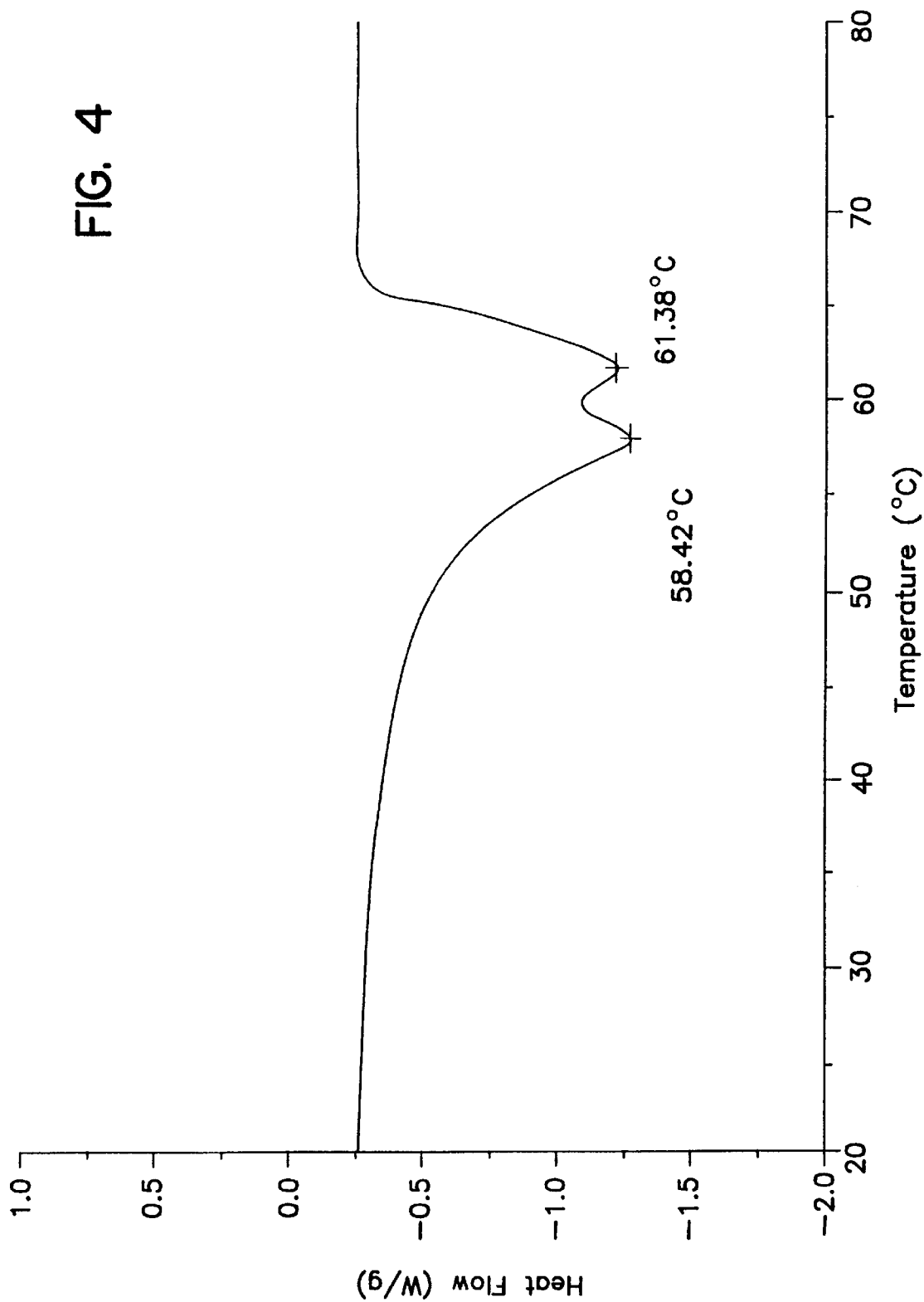
FIG. 4 depicts the differential scanning colorimetry for a polymer composition that exhibits a two peak phase separation.

First, a polymer composition was prepared as follows: 59.5 wt % poly(caprolactone) possessing a 80,000 molecular weight, 25.5 wt % of poly(ethylene oxide) possessing a 5,000,000 molecular weight, and 15 wt % of poly (oxyethylene 40 stearate) were blended at a temperature range of 65–95° C. using a mixer to produce a homogeneous blend. Second, the blend was extruded at 80–90° C. and pelletized at 25° C. using an extruder and pelletizer. Then, the pellets were hot-pressed to provide a membrane analyzed by differential scanning colorimetry, DSC, by following the differented scanning calorimety procedures in *Encyclopedia of Polymer Science and Engineering*, Supp. Vol pp 702–711, (1989), lnterscience-Publication. Accompanying FIG. 1 is the DSC thermogram for the dry blend, showing three distinguished melting peaks, associated to each individual component, as follows: poly(oxyethylene 40 stearate) peak at 49.5° C., poly(caprolactone) peak at 59.2° C., and poly(oxyethylene oxide) peak at 70.1° C. The "x" axis is the temperature in degrees centigrade, and the "y" axis is the heat flow in (W/g) wherein W is watts and g is grams. However, the hot-melt blend with the same composition shows only one melting peak at 62.0° C., indicating a good miscibility of the three components as seen in FIG. 2. The hot-melt blend membrane exposed to elevated temperature of 104° C. for more than two hours still shows only one peak as seen in FIG. 3. The peak of FIG. 3 is in sharp contrast with a polymer composition comprising poly(caprolactone) of 80,000 molecular weight, poly(ethylene oxide) of 5,000,000 molecular weight and poly(ethylene glycol) of 3350 molecular weight to provide a 59.5 wt %–25.5 wt %–15 wt % composition that shows double peaks in FIG. 4 indicating phase separation. Thus FIGS. 1 to 4 demonstrate the unexpected property for the polymer composition provided by this invention.

EXAMPLE 2

The procedure of Example 1 was followed in this example for providing a membrane comprising 63 wt % poly (caprolactone), 27 wt % poly(ethylene oxide), and 10 wt % poly(oxyethylene 40 stearate).

EXAMPLE 3

The procedure of Example 1 is repeated in this example for providing a membrane comprising 58 wt % poly (caprolactone), 32 wt % poly(ethylene oxide) and 10 wt % poly(oxyethylene 40 stearate).

EXAMPLE 4

The procedure of Example 1 is repeated in this example for providing a membrane comprising 67.9 wt % poly (caprolactone), 29.1 wt % poly(ethylene oxide) and 3 wt % poly(oxyethylene 40 stearate).

EXAMPLE 5

The procedure of Example 1 is repeated in this example for providing a membrane comprising 62.3 wt % poly (caprolactone), 27 wt % poly(ethylene oxide), 10 wt % poly(oxyethylene 40 stearate), and 0.7 wt % of a member selected from the group consisting of lactose, or fructose, or Cab-o-Sil, a colloidal silicon dioxide as a nucleating agent.

EXAMPLE 6

The procedure of Example 1 is repeated in this example for providing a membrane comprising 70 wt % poly (caprolactone), 27 wt % poly(ethylene oxide) and 3 wt % poly(oxyethylene)-poly(oxypropylene) block copolymer Pluronic F-108.

EXAMPLE 7

The procedure of Example 1 is followed for providing a composition comprising 70 wt % poly(caprolactone), 20 wt % poly(ethylene oxide) and 10 wt % poly(oxyethylene-co-oxypropylene) Pluronic F-108.

EXAMPLE 8

The procedure of Example 1 is followed for providing a composition comprising 63 wt % poly(caprolactone), 27 wt % poly(ethylene oxide), and 10 wt % poly(oxyethylene-co-oxypropylene) Pluronic F-108.

EXAMPLE 9

The procedure of Example 1 is followed for providing a composition comprising 56 wt % poly(coprolactone), 24 wt % poly(ethylene oxide), and 20 wt % poly(oxyethylene-co-oxypropylene) identified as Pluronic F-108.

EXAMPLE 10

The procedure of the above examples are followed for providing a polymeric composition comprising 40–85 wt % poly(caprolactone), 5–40% poly(ethylene oxide), and 2–20 wt % poly(oxyethylene-co-oxypropylene).

EXAMPLE 11

A dosage form comprising an injection-molded membrane consisting of the poly(caprolactone), poly(ethylene oxide) and poly(oxyethylene 40 stearate) composition that surrounds an internal space with an opened mouth and a closed bottom is charged at its bottom with a push composition and then with a drug composition at the opened mouth. The push composition comprises 58.75 wt % sodium carboxymethylcellulose, 30.00 wt % sodium chloride, 5.00 wt % hydroxypropylmethylcellulose, 5.00 wt % hydroxypropylcellulose, 1.00 wt % red ferric oxide, and 0.25 wt % magnesium stearate. The drug composition comprises 66.70 wt % gemfibrozil, 14.30 wt % Acid-Di-Sol, a sodium croscarmellose, 9.50 wt % poly(ethylene oxide); 5.00 wt % lecithin, 3.00 wt % hydroxypropylmethylcellulose, 1.00 wt % Cab-O-Sil, a colloidal silicon dioxide, and 0.50 wt % magnesium stearate. The opened mouth of the dosage form is crimped to a 15 mil (0.381 mm) orifice to provide an osmotic dosage form.

EXAMPLE 12

A dosage form comprising an injection-molded membrane comprising poly(caprolactone), poly(ethylene) and poly(oxyethylene-co-oxypropylene) is prepared by following the procedure of Example 11. The dosage form comprises a composition comprising a drug, an osmagent and an osmopolymer, as disclosed in U.S. Pat. No. 4,612,008. The drug composition comprises 50% sodium diclofenac, 46% poly(ethylene oxide) having a 100,000 molecular weight, 2% sodium chloride, 1 magnesium stearate and 1% poly(vinylpyrrolidone) binder.

EXAMPLE 13

Another dosage form provided by the invention comprises a housing consisting of a first membrane section and a second membrane section. The first section and the second section are designed to close in telescopic arrangement with each other. The membrane forming the first section is injected-molded from a poly(caprolactone), or poly(vinylacetate) composition and the second section is injected-molded from a poly(caprolactone), poly(ethylene oxide), and poly(oxyethylene 40 stearate) composition. The first section comprises a therapeutic composition for administering to an animal or to a human. The second section is a means for closing the first section as a cap during storage. The second section is a means for opening the dosage form, when the dosage form is in operation in a fluid environment of use for dispensing a therapeutic composition from the first section to the environment. The second section comprises an osmotic layer comprising 58.75 wt % sodium carboxymethyl cellulose, 30% sodium chloride, 5.00 wt % hydroxypropylcellulose, 5.00 wt % hydroxyethylcellulose, 1.00 wt % red ferric oxide, and 0.25 wt % magnesium stearate. The osmotic layer is positioned against the bottom of the second section. Next, a barrier layer comprising 95.00 wt % stearic acid and 5.00 wt % hydroxypropylmethylcellulose is positioned on the section in bilayer arrangement with the osmotic layer. The dosage form is assembled by the smaller opened end fitted inside the layer open end and compressed together until the first section and the second section fit together tightly. A dosage forms made by solvent techniques is disclosed in U.S. Pat. No. 5,312,388 issued to Wong, Theeuwes, and Larsen and assigned to the ALZA Corporation. Conventional injection-molding machines as disclosed in *Encyclopedia of Polymer Science and Engineering*, Vol. 8, Injection-Molding, pp 102 to 138, 1987 can be used for the purpose of this invention.

Further Disclosure of the Invention

The phrase therapeutic agent and drug are used interchangeably herein, and they refer to an agent, drug compound, composition of matter or mixture thereof which provides a therapeutic, beneficial effect. The term agent includes pesticides, herbicides, germicides, biocides, algicides, rodenticides, fungicides, insecticides, antioxidants, plant-growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses, and pigs; laboratory animals such as mice, rats and guinea pigs; fish; reptiles, zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocold systems, the alimentary and excretory systems, the histamine system, and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetrics, polypeptides and proteins capable of eliciting physiological responses diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents for use by this invention are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine sulfate, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, pednisolone, 17-β-hydroxyprogesterone acetate, 19-norprogesterone, norgestrel, norethindrone, norethisterone, norethiederone, progesterone, norgesterone, norethisterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, enitabas, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captropril, mandol, quabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidofiazine, tiapamil, gallopamil, amlodipine, mioflazine, lisinopril, enalapril, captopril, ramipril, endlapriat, famotidine, nizatidine, sucralfate, etindinine, tetratolol, minoxidil, chlordiazepoxide, diazepam, amitriptylin, and imipramine. Further examples are proteins and proteins which include, but are not limited to, insulin, colchicine, glucagon, thyroid stimulating hormone, parathyroid and pitutary hormones, calcitonin, renin, prolactin, corticotrophin, thyrotropic hormone, follicle stimulating hormone, chorionic gonadotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and procine growth hormone, fertility inhibitors such as the prostaglandins, fertility promoters, growth factors, and human pancreas hormone releasing factor.

It is to be understood that more than one therapeutic agent can be incorporated into the dosage form of this invention, and the use of the expressions therapeutic agent or drug in no way excludes the use of two or more such therapeutic agents or drugs. The therapeutic agent can be in a wide variety of chemical and physical forms, such as uncharged molecules, components of molecular complexes, nonirritating pharmaceutically acceptable salts, therapeutic derivatives of the therapeutic agent such as ethers, esters, amides, etc, therapeutic derivatives of the therapeutic agent that are easily hydrolyzed by the body pH, and enzymes, are included in this invention. The amount of therapeutic agent in the dosage form is an amount necessary to produce the desired therapeutic response. In practice, this will vary widely depending upon the particular therapeutic agent, the site of delivery, the severity of the medical condition, and the desired therapeutic effect. Thus, often it is not practical to define a particular therapeutic range for a therapeutically effective dose of the therapeutic active agent incorporated into the dosage form, however, the dosage form generally will contain 0.1 mg to 1.0 g of the therapeutic agent. The therapeutically active drugs are disclosed in *Pharmacotherapy*, Vol. 8, pp 147–157 (1988); *Drugs*, Vol. 30, pp 333–354, (1985); *Remington's Pharmacological Basis of Therapeutics* by Goodman and Gilman, 4$^{th}$ Ed., 1970, published by The Man Million Company, London.

The term osmagent as used herein also includes osmotically effective solute, osmotically effective compound, and osmotic agent. The osmotically effective compounds that can be used for the purpose of this invention include inorganic and organic compounds that exhibit an osmotic pressure gradient across a semipermeable membrane against an external fluid. Osmotically effective compounds useful for the present purpose include magnesium sulfate, magnesium chloride, sodium chloride, lithium chloride, potassium sulfate, sodium carbonate, sodium sulfate, lithium sulfate, potassium chloride, sodium sulfate, calcium bicarbonate, calcium sulfate, potassium acid phosphate, calcium lactate, mannitol, urea, inositol, magnesium succinate, tartaric acid, carbohydrates, raffinose, sucrose, glucose, lactose monohydrate, and mixtures thereof. The osmotically effective solute can be in any physical form such as particle, crystal, pellet, tablet, strip, ground, pulverize, film, or granules. The osmotically effective solutes and procedures for measuring osmotic pressures are dissolved in U.S. Pat. No. 5,232,705.

The push composition, in a dosage form of osmotic design and construction, contains an expandable means also known as osmopolymer, hydrogel, and expandable member in the dosage form for the purpose of this invention comprise a push composition that interacts with water, or aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncrosslinked or crosslinked. The swellable, hydrophilic polymers are, in one presently preferred embodiments, lightly crosslinked, such as cross-links formed by covalent or ionic bonds. The osmopolymers can be of plant, animal or synthetic origin. Hydrophilic polymers suitable for the present purpose include poly(hydroxyalkylmethacrylate); poly (vinylpyrrolidone); anionic and cationic hydrogels; polyelectrolyte complexes, poly(vinyl alcohol) having a low acetate residual, crosslinked with formaldehyde, or glutaraldehyde; a mixture of methyl cellulose, crosslinked agar and carboxymethyl cellulose, a water insoluble, water swellable copolymer produced by forming a dispersion of finely divided copolymer of maleic anhydride with styrene, ethylene, propylene, butylene or isobutylene crosslinked with from 0.0001 to about 0.5 moles of polyunsaturated crosslinking agent per mole of maleic anhydride in the copolymer; water swellable polymers of N-vinyl lactams, and the like.

Other osmopolymers include polymers that form hydrogels such as Carbopol® acidic carboxy polymers, the sodium salt of Carbopol® acidic carboxy polymers and other metal salts; Cyanamer® polyacrylamides; crosslinked water swellable indene maleic anhydride polymers; Goodrite® polyacrylic acid, and the sodium and other metal salts; Polyox® polyethylene oxide polymers; starch graff copolymers; Aqua-Keeps® acrylate polymers; diester crosslinked polyglucan, and the like. Representative polymers that form hydrogels are known to the prior art in U.S. Pat. No. 3,865,108 issued to Hartop; U.S. Pat. No. 4,207,893 issued to Michael's, and in *Handbook of Common Polymers*, by Scott and Roff, published by the Chemical Rubber, CRC Press, Cleveland, Ohio.

Other osmopolymers that can be present in the first layer include agarose, alginates, amylopectin, arabinoglactan, carregeen, eucheuma, fucoidan, furcellaran, gelatin, guar gum, gum agar, gum arabic, gum ghatti, gum karaya, gum tragacanth, hypnea, laminarin, locust bean gum, pectin, polyvinyl alcohol, polyvinyl pyrrolidone, propylene glycol aginates, N-vinyl lactam polysaccharides, xanthan gum, and the like. The osmopolymers are known in *Controlled Release System*. Fabrication Technology, Vol. 11, pg 46 (1988), published by CRC Press, Inc.

Inasmuch as the foregoing specification comprises preferred embodiments of the invention, it is understood that variations and modification may be made herein, in accordance with the inventive principles disclosed, without departing from the scope of the invention.

We claim:

1. An injection molded membrane, formed as a single phase in the absence of an organic solvent, comprising 40–85 weight percent poly(caprolactone), 5–40 weight percent poly(alkylene oxide), and 2–20 weight percent of a polymer selected from the group consisting of poly(oxyethylenated fatty acids), poly(oxyethylenated fatty acid esters) and poly(oxyethylene)-co-poly(oxypropylene) block copolymers.

2. The injection molded membrane of claim 1 wherein the poly(alkylene oxide) is poly(ethylene oxide) and the polymer is selected from the group consisting of poly(oxyethylene lauric acid), poly(oxyethylene mryistic acid), poly(oxyethylene oleic acid), poly(oxyethylene palmitic acid), poly(oxyethylene stearic acid), poly(oxyethylene laurate), poly(oxyethylene myristate), poly(oxyethylene oleate), poly(oxyethylene palmitate), poly(oxyethylene stearate, and poly(oxyethylene)-co-poly(oxypropylene) block copolymer.

3. The injection molded membrane of claim 2 wherein the polymer is poly(oxyethylene stearate).

4. The injection molded membrane of claim 2 wherein the polymer is poly(oxyethylene 40 stearate).

5. The injection molded membrane of claim 2 wherein the polymer is poly(oxyethylene)-co-poly(oxypropylene) block copolymer.

6. The injection molded membrane of claim 2 wherein the polymer is poly(oxyethylene)-co-poly(oxypropylene) block copolymer having a molecular weight of 1,100–25,000.

7. The injection molded membrane of claim 1 wherein the membrane is semipermeable.

8. The injection molded membrane of claim 1 wherein the membrane is water permeable.

* * * * *